United States Patent [19]

Lanham et al.

[11] 4,072,572

[45] Feb. 7, 1978

[54] *E. COLI* DETECTION BROTH FOR CLINICAL USE WITH AUTOMATED MICROBIAL ANALYZER

[75] Inventors: James W. Lanham, St. Louis; Gregory D. Rodgers, Florissant, both of Mo.; Michael C. Meyer, O'Fallon, Ill.

[73] Assignee: McDonnell Douglas Corporation, St. Louis, Mo.

[21] Appl. No.: 682,651

[22] Filed: May 3, 1976

[51] Int. Cl.$^2$ .............................................. C12K 1/06
[52] U.S. Cl. ................................................... 195/100
[58] Field of Search ................................. 195/99–103, 195/103.5 R

[56] References Cited

PUBLICATIONS

Robert Bailey and Elvyn Scott, Diagnostic Microbiology, Second. Ed., The C. V. Mosby Company, 1966, pp. 26, 295–296.

*Primary Examiner*—Lionel M. Shapiro
*Assistant Examiner*—Robert J. Warden
*Attorney, Agent, or Firm*—Gravely, Lieder & Woodruff

[57] ABSTRACT

A medium for the detection and identification of *Escherichia coli* (*E. coli*) in urine samples.

The medium employs para-coumaric acid, saponin and 3,4-dihydroxybenzoic acid to inhibit growth of unwanted microorganisms and thus eliminate false positive test results.

8 Claims, No Drawings

E. COLI DETECTION BROTH FOR CLINICAL USE WITH AUTOMATED MICROBIAL ANALYZER

BACKGROUND OF THE INVENTION

The medium of this invention is an improved medium designed for use with the optical detection system disclosed in U.S. applications Ser. Nos. 255,533 filed May 22, 1972 now abandoned and 461,249 filed Apr. 16, 1974 now U.S. Pat. No. 3,963,355 and in the improved devices disclosed and claimed in applications filed on even date herewith by Charles, Jones, Staples and Wiegner entitled AUTOMATED MICROBIAL ANALYZER and MACHINE AND PROCESS FOR READING CARDS CONTAINING MEDICAL SPECIMENS. These applications describe mechanism and apparatus suitable for analyzing specimens for specific microorganisms using a plastic tray or card which contains a series of dried culture media contained in separate but connected wells, each of the media being specific to a single organism. When the sample is inserted into the card, mixed with the media in the wells, and incubated in the machine; the organism (or organisms) present in the specimen interacts with the culture medium specific to that organism and produces a change in the medium which is read by the machine to indicate the presence of that organism. The change in the medium involves a change in the light transmitting properties of the medium, i.e., a color change or change in turbidity. The change may be caused by metabolic activity of the organism, which, for example, may cause production of acid and a change in pH which causes a color change in a pH sensitive indicator in the medium. The change in the light transmitting properties of the medium also could be caused by a precipitate forming in the medium due to metabolic activity of the organism or it could be caused by growth of the organism.

The specific media designed for use in the aforesaid cards are all designed to favor growth of one microorganism and to inhibit growth of other organisms, are capable of being freeze dried, and can function in the low $O_2$ environment of the wells of the card described in detail in said copending applications "AUTOMATED MICROBIAL ANALYZER" and "MACHINE AND PROCESS FOR READING CARDS CONTAINING MEDICAL SPECIMENS".

The medium of this invention is designed to favor growth of the gram negative bacterium *Escherichia coli* (*E. coli*). It contains sugar sources which are fermented selectively by *E. coli* to produce acids and further contains a pH sensitive indicator, reduced Aniline Blue, which turns from clear to a blue color in response to the change in pH produced by such acid production. The medium also contains a combination of inhibitors of other gram negative organisms, principally Klebsiella. The combination of inhibitors includes coumaric acid, 3,4-dihydroxy-benzoic acid, and saponin. This combination inhibits Klebsiella and allows *E. coli* to grow. The medium also contains surfactants as inhibitors for gram positive organisms.

SUMMARY OF THE INVENTION

This invention involves a medium for the detection and identification of *E. coli* in urine samples.

The medium employs sources of nutrients favorable to the production of *E. coli*, a biological pH indicator responsive to acid production by the *E. coli*, and a combination of para-coumaric acid, saponin, and 3,4-dihydroxybenzoic acid to inhibit growth of Klebsiella, as well as other inhibitors to inhibit growth of gram positive microorganisms.

DETAILED DESCRIPTION

The detection medium of the present invention contains per liter from about 15.1 gm to 28.0 gm nutrients, about 15 ml to about 35 ml of an indicator which indicates the production of acid by *E. coli* organism, about 1.5 gms to about 4.5 gm surfactants to inhibit the growth of gram positive organisms, and about 0.05 gm to about 1.5 gm p-coumaric acid, about 0.05 gm to about 1.5 gm 3,4-dihydroxybenzoic acid, about 0.75 gm to about 1.25 gm saponin, which, in combination inhibit the growth of other coliform-like organisms (principally Klebsiella) which normally give positive results in tests for *E. coli*.

The nutrient portion of the medium contains from about 4.0 to about 6.0 gm/l lactose, from about 4.0 to about 6.0 gm/l L-arabinose, and from about 4.0 to about 6.0 gm/l Gelysate, and from about 0.75 gm to about 1.25 gm yeast extract.

Gelysate is made by BBL and is a gelatine hydrolysate made by pancreatic digestion characterized by a low cystine and trytophane content. It is a conventionally available item of commerce commonly used in media.

Most strains of *E. coli* ferment lactose to produce an acid. L-arabinose is used in the detection medium because it is able to be fermented by the less than 10% of the strains of *E. coli* that cannot readily ferment lactose. Thus this medium, using the combination of sugars, will detect all strains of *E. coli*.

Suitable substitutes for Gelysate are Trypticase, Phytone and Polypeptone.

The Bile Salts Mixture, available from BBL, is used to inhibit the growth of gram positive organisms. Bile Salts Mixture contains bile extractives and is a mixture of surfactants which inhibit gram positive organisms, such as Bacillus species. Other suitable surfactants include Bile Salts No. 3, Taurocholic Acid, etc. Bile Salts Mixture is a commercially available material commonly used in media to inhibit gram positive organisms.

A combination of 3,4-dihydroxybenzoic acid, saponin, and para-coumaric acid are used to inhibit the growth of Klebsiella and other coliform-like organisms. The ortho- and meta-forms of coumaric acid can also be used. However, these forms do not inhibit coliform-like organisms as effectively as does the para-form.

In copending application of Serial No. 682,252 James W. Lanham Ralph A. Wilkinson and Leodis Woods entitled *E. COLI* IDENTIFICATION BROTH, filed of even date herewith, is disclosed a medium for the detection of *E. coli* which contains only coumaric acid as an inhibitor. It has been determined that when a mixture of organisms are present, i.e. *E. coli* and Klebsiella, a phenomenon occurs which is not totally understood. Under these circumstances the coumaric acid inhibited the growth of both Klebsiella and *E. coli*. It is postulated that the Klebsiella converted the coumaric acid into compounds which also inhibited *E. coli*. By adding the saponin and the 3,4-dihydroxybenzoic acid, this effect is prevented and only the Klebsiella is inhibited and and *E. coli* is allowed to grow and act metabolically on the lactose and L-arabinose.

The indicator to be used in this detection medium is a biological pH indicator which undergoes a change of color at a pH of about 6.8 to 7.0. Reduced Aniline Blue is the preferred indicator, as this indicator undergoes a color change from clear to blue that is readily detectable by the mechanism of application entitled AUTOMATED MICROBIAL ANALYZER. When the Aniline Blue is reduced in accordance with the process of application of Clifton Aldridge and Michael Meyer entitled SENSITIVE pH INDICATOR, filed on even date herewith, stable, or clear liquid is obtained which turns blue at pH 6.8-7. No other indicators are known which have this effect at this pH range.

Yeast extract, or other suitable biological extract, may also be added as a vitamin source. From about 0.95 to about 1.05 gm/l yeast extract can be used. The yeast extract is available from BBL and is a water soluble extract of autolysed yeast cells. Such products are conventionally available from many sources.

The pH of the medium should be held at 7.5 prior to use.

PREPARATION OF E. COLI BROTH

One hundred milliliters of 2x medium is prepared by mixing 0.2 gm p-coumaric acid and 0.2 gm 3,4-dihydorxybenzoic acid with 3 ml 1NNaOH/100 ml media to ¼ required volume distilled water. This mixture is heated until all solids are in solution. The solution is Q.S. to 95 ml with distilled water and 1.0 gm Gelysate, 1.0 gm. lactose, 1.0 gm L-arabinose, 0.6 gm Bile Salts Mixture and 0.2 mg yeast extract are added. The pH is adjusted to 6.2 and 5 ml of Reduced Aniline Blue Indicator are added with 0.2 gm saponin. The pH is checked and corrected to 7.5 by adding a base if necessary. The solution is filter sterilized, placed in a sterile container and labeled. The foregoing solution is double strength. When it is rehydrated at a normal single strength concentration, it contains the following per liter:
  about 1 gm para-coumaric acid
  about 1 gm 3,4-dihydroxybenzoic acid,
  about 1 gm saponin,
  about 5 gm lactose,
  about 5 gm L-arabinose,
  about 5 gm nitrogen source,
  about 1 gm yeast extract,
  about 3 gm gram-positive inhibitor,
  about 25 ml biological pH indicator, and distilled water to 100%.

OPERATION

The double strength medium prepared as hereinbefore shown is used. The preparation is loaded into the wells of the urine screening card described in application entitled AUTOMATED MICROBIAL ANALYZER, freeze dried and the card is taped to protect the media. The amount of double strength medium is equivalent to one-half the volume of the well. Thus, when the remaining volume of the well is filled with a urine sample, the medium will be rehydrated at a normal single strength concentration, at which concentration it is functional.

This medium detects concentrations of E. coli of $10^3$ cells/ml in 12 hours. Slightly longer detection time is required for lower concentrations.

What is claimed is:

1. A composition for selectively identifying E. coli comprising:
   a. a source of nutrients,
   b. an indicator to show the presence of E. coli organism and,
   c. means for inhibiting the growth of other coliform-like organisms which normally give positive results in tests for E. coli comprising a combination of coumaric acid, 3,4-dihydroxybenzoic acid, and saponin.

2. The composition of claim 1 wherein the inhibiting means includes para-coumaric acid.

3. The composition of claim 1 wherein the inhibiting means is about 0.05 to about 1.50 gm/l para-coumaric acid, about 0.05 to about 1.50 gm/l 3,4-dihydroxybenzoic acid, and about 0.75 to about 1.25 gm/l saponin.

4. The composition of claim 1 wherein the indicator is reduced Aniline Blue.

5. The composition of claim 4 wherein said composition has a pH of about 7.5 and is colorless and wherein the indicator changes from colorless to blue as the pH goes from about 7.5 to about 6.8-7 to indicate the presence of E. coli.

6. The composition of claim 1 including a combination of lactose and L-arabinose as sources of sugar which are fermented by E. coli.

7. A composition for selectively identifying E. coli comprising per liter:
   a. from about 0.05 to about 1.50 gm para-coumaric acid,
   b. from about 0.05 to about 1.50 gm 3,4-dihydroxybenzoic acid,
   c. from about 0.75 to about 1.25 gm saponin,
   d. from about 4.0 to about 6.0 gm lactose,
   e. from about 4.0 to about 6.0 gm L-arabinose,
   f. from about 4.0 to about 6.0 gm nitrogen source,
   g. from about 0.75 to about 1.25 gm yeast extract,
   h. from about 1.5 to about 4.5 gm gram positive inhibitor,
   i. from about 15 to about 35 ml biological pH indicator, and
   j. distilled water to 1 liter.

8. A composition for selectively identifying E. coli comprising per liter:
   a. about 1 gm para-coumaric acid,
   b. about 1 gm 3,4-dihydroxybenzoic acid,
   c. about 1 gm saponin,
   d. about 5 gm lactose,
   e. about 5 gm L-arabinose,
   f. about 5 gm nitrogen source,
   g. about 1 gm yeast extract,
   h. about 3 gm gram positive inhibitor,
   i. about 25 ml biological pH indicator, and
   j. distilled water to 100%.

* * * * *